United States Patent [19]

Bulteau et al.

[11] 4,166,060

[45] Aug. 28, 1979

[54] PROCESS FOR PRODUCING ENAMINES

[75] Inventors: Gérard Bulteau, Paris; Jacques Acher, Itteville; Jean-Claude Monier, Lardy, all of France

[73] Assignee: Societe d'Etudes Scientifiques et Industrielles de l'Ile-de-France, Paris, France

[21] Appl. No.: 863,062

[22] Filed: Dec. 21, 1977

[30] Foreign Application Priority Data

Jun. 12, 1975 [FR] France ................................. 7518344

Related U.S. Application Data

[62] Division of Ser. No. 694,877, Jun. 11, 1976, Pat. No. 4,077,976.

[51] Int. Cl.² ........................................... C07D 207/08
[52] U.S. Cl. ............................. 260/326.2; 260/239 B; 546/246; 260/239 BF

[58] Field of Search ....................... 260/326.2, 326.43

[56] References Cited

PUBLICATIONS

Smith, "The Chem. of Open-Chain Organic Nitrogen Compounds," vol. I, Bejamin, Inc., N.Y., (1965), pp. 329 & 330.

Morrison et al., pp. 944 & 945, Allyn & Bacon, Boston, (1966).

*Primary Examiner*—Donald G. Daus
*Assistant Examiner*—D. B. Springer
*Attorney, Agent, or Firm*—Frank M. Nolan

[57] ABSTRACT

Enamines which are employed to obtain benzamides effective in the treatment of emesis are produced by efficient processes.

2 Claims, No Drawings

PROCESS FOR PRODUCING ENAMINES

This application is a division of the co-pending application Ser. No. 694,877, filed June 11, 1976, now U.S. Pat. No. 4,077,976, issued Mar. 7, 1978.

The enamines of this invention may be employed in the production of benzamides useful in the treatment of emesis in mammals such as the benzamides described in Miller et al. U.S. Pat. No. 3,342,826.

The enamines of this invention have the following formula:

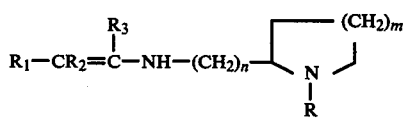

in which:

R may be a $C_{1-5}$ alkyl group or $C_{2-5}$ alkenyl group, containing or not containing a reactive function such as alcohol, thioalcohol, ketone, thioketone, ether or thioether, $R_1$ may be an alkyl group with 1 to 5 carbon atoms, or an alkyl carboxylate group, or an acyl group, $R_2$ may be hydrogen or an alkyl group with 1 to 5 carbon atoms, $R_3$ may be an alkyl group with 1 to 5 carbon atoms, or an alkyl carboxylate group, $R_2$ and $R_3$ may be joined together via a methylene group, and n and m may have the values 1, 2, 3, as well as their dextrorotary and levorotary isomers, their acid addition salts, their quaternary ammonium salts, and a process for their preparation.

The compounds of the invention may be used for example to synthesize substances having valuable therapeutic properties, i.e., antiemetic benzamides.

The compounds of the invention may be prepared by reacting ketones having a mobile hydrogen atom in the α-position, aliphatic β-diketones, or β-ketone esters with an amine of the following general formula:

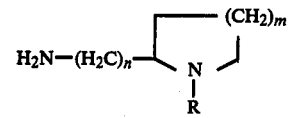

in which: n, m and R have the previously given meanings.

The example given hereinafter to illustrate the invention is not limiting:

Methyl N-(1-ethyl-2-pyrrolidylmethyl)-3-aminocrotonate hydrochloride 38.4 g (0.3 mole) of N-ethyl-2-aminomethylpyrrolidine and a drop of hydrochloric acid d=1.18 were added into a 250 ml flask provided with a stirrer, a thermometer, a condenser and a dropping funnel; 34.8 g (0.3 mole) of methyl acetoacetate were added drop by drop. The temperature reached 54° C. by the end of the introduction. The mixture was next allowed to return to ambient temperature while stirring, and 150 ml of methylene chloride and 5 g of magnesium sulphate were then added. The mixture was stirred for one hour, filtered, the solvent was vaporated in vacuo, and the residue was distilled. 55 g of methyl N-(1-ethyl-2-pyrrolidylmethyl)-3-aminocrotonate were obtained. (Yield: 81.1%; boiling point—3 mm/Hg: 132°–134° C.).

55 g (0.24 mole) of methyl N-(1-ethyl-2-pyrrolidylmethyl)-3-aminocrotonate, 250 ml of acetone and sufficient amount of ethanolic hydrochloric acid to bring the pH to 1 were added into a 500 ml beaker, while stirring the mixture. The product was allowed to crystallize out and was then filtered and dried in an oven at 50° C.

60.8 g of methyl N-(1-ethyl-2-pyrrolidylmethyl)-3-aminocrotonate hydrochloride were obtained. (Yield: 95.2%; m.p. 140° C.)

What is claimed is:

1. The process of producing methyl (N-1-ethyl 2-pyrrolidylmethyl) 3-aminocrotonate or its hydrochloride, said process comprising the step of treating in the presence of a catalytic amount of hydrochloric acid 1-ethyl 2-aminoethyl pyrrolidine with methyl acetoacetate.

2. The process of producing methyl N-(1-ethyl 2-pyrrolidylmethyl) 3-aminocrotonate hydrochloride, said process comprising producing said crotonate in accordance with claim 1 and reacting said crotonate with ethanolic hydrochloric acid.

* * * * *